United States Patent [19]

Leconte

[11] Patent Number: 4,613,702

[45] Date of Patent: Sep. 23, 1986

[54] ALDEHYDE PRODUCTION BY HYDROCARBONYLATION OF ORGANIC HALIDES

[75] Inventor: Philippe Leconte, Lyons, France

[73] Assignee: Rhone-Poulenc Specialites Chimiques, Courbevoie, France

[21] Appl. No.: 734,133

[22] Filed: May 15, 1985

[30] Foreign Application Priority Data

May 15, 1984 [FR] France ................. 84 07697

[51] Int. Cl.$^4$ .................. C07C 45/49; C07C 45/00
[52] U.S. Cl. ........................... 568/490; 568/428; 568/429; 568/437; 568/454; 568/455
[58] Field of Search ............ 568/490, 428, 437, 454, 568/455

[56] References Cited

U.S. PATENT DOCUMENTS 3,960,932  6/1976  Heck ................................. 568/490
3,996,288  12/1976  Yukata et al. ..................... 568/490
4,338,467  7/1982  Takano et al. .................... 568/428

FOREIGN PATENT DOCUMENTS 0034430  8/1981  European Pat. Off. ........... 568/428
2364039  7/1974  Fed. Rep. of Germany ...... 568/428
3,242,582  5/1984  Fed. Rep. of Germany ...... 568/428
0004319  1/1980  Japan ................................ 568/428
0164736  9/1984  Japan ................................ 568/428
0161340  12/1984  Japan ................................ 568/490

*Primary Examiner*—Werren B. Lone
*Attorney, Agent, or Firm*—Burns, Doane, Swecker & Mathis

[57] ABSTRACT

Aldehydes are facilely prepared in high yields by catalytically hydrocarbonylating an organic halide with gaseous admixture of hydrogen and carbon monoxide in the presence of a neutralizing agent for the hydrogen acid produced thereby, said hydrocarbonylation being carried out in an inert, liquid carboxylic acid reaction medium, i.e., a liquid carboxylic acid which is inert under the reaction conditions of temperature and pressure.

25 Claims, No Drawings

ALDEHYDE PRODUCTION BY HYDROCARBONYLATION OF ORGANIC HALIDES

BACKGROUND OF THE INVENTION

1. Field of the Invention

The present invention relates to the preparation of aldehydes, and, more especially, to the preparation of aldehydes by hydrocarbonylation of organic halides.

2. Description of the Prior Art

The hydrocarbonylation of organic halides has served as impetus for many investigations with a view to the development of an industrial process for the preparation of aldehydes. Thus, in Hungarian Pat. No. 150,412 (*Chemical Abstracts*, 60, 2847c) it has been recommended to effect hydrocarbonylation of organic halides (for example, octyl bromide and benzyl chloride) by reaction of the latter compounds with a mixture of carbon monoxide and hydrogen, under pressure, in the presence of dicobaltoctacarbonyl in an acetone/water mixture. Under these conditions the yields are often moderate and the reaction time on the order of 4 hours restricts the productivity of the process despite the use of high temperatures and pressures and a relatively large amount of catalyst.

In order to reduce the temperature and time of reaction it has been proposed, in French patent application No. 73/46,069, published under No. 2,211,451, and in Japanese patent application published under No. 75/149,610, to prepare phenylacetaldehyde and substituted derivatives thereof by hydrocarbonylation of benzyl halides in the presence of a catalyst consisting of a transition metal derivative, particularly dicobaltoctacarbonyl, in a water-immiscible organic solvent/water pair, said reaction being carried out in the added presence of a tertiary amide (dimethyl- or diethylformamide or acetamide) and a basic agent which serves to neutralize the hydrogen acid produced thereby (weak-acid salts of alkali metals or alkaline earth metals; alkali metal hydroxides; organic bases). Although the presence of the tertiary amide makes it possible to lower the temperature and to increase the yield of phenylacetaldehyde, the latter does not exceed 60% in the best of cases and the pressures employed remain high (on the order of 13.7 to 19.6 MPa). Furthermore, this process has the disadvantage of requiring the use of a large amount of amide (1 mole per mole of benzyl halide) and a still relatively high amount of catalyst (e.g., 0.26 mole of dicobaltoctacarbonyl per mole of benzyl halide).

In published European patent application No. 0,034,430 an attempt has been made to solve the problem of the hydrocarbonylation of arylmethyl halides to arylacetaldehydes by carrying out the reaction in a nitrile, optionally combined with a hydrocarbon, in the presence of a cobalt derivative and a base. The substitution of the nitrile/hydrocarbon system for the water-immiscible organic solvent/water system results in the production of good yields of arylacetaldehydes in the presence of small amounts of catalyst. Nevertheless, it is found that the reaction time remains on the order of 2 to 3 hours.

In capsule summary, despite the efforts carried out since the publication of Hungarian Pat. No. 150,412, serious industrial need continues to exist for a process for the preparation of aldehydes by hydrocarbonylation of organic halides which makes it possible to obtain both good yields of aldehydes and good productivity without requiring the use of a large amount of hydrocarbonylation catalyst and without resorting to high temperatures and/or pressures. Cf. U.S. Pat. No. 4,338,467; CA, 94, 46969s (1981).

SUMMARY OF THE INVENTION

Accordingly, a major object of the present invention is the provision of an improved process for the hydrocarbonylation of organic halides which provides high yields of aldehydes and is otherwise free from those disadvantages and drawbacks to date characterizing the state of this art.

Briefly, the present invention features a process for the preparation of aldehydes by reaction of an organic halide with a gaseous mixture of hydrogen and carbon monoxide, in the presence of a hydrocarbonylation catalyst and an agent for neutralizing the hydrogen acids formed, in which the hydrocarbonylation reaction is carried out in a liquid carboxylic acid which is inert under the temperature and pressure conditions employed.

DETAILED DESCRIPTION OF THE INVENTION

More particularly according to the present invention, featured is a process for the preparation of aldehydes having the general formula:

$$R-CH_2-CHO \qquad (I)$$

in which R denotes a hydrogen atom, an alkyl radical or an aryl radical, by hydrocarbonylation, in an inert carboxylic acid reaction medium, utilizing a mixture of carbon monoxide and hydrogen, of organic halides having the general formula:

$$R-CH_2X \qquad (II)$$

in which R is as defined above and X denotes a halogen atom, specifically chlorine, bromine or iodine, in the presence of a hydrocarbonylation catalyst and an agent for neutralizing the hydrogen acids formed.

In the aforesaid formulae (I) and (II), R is advantageously a straight or branched chain alkyl radical containing from 1 to 20 carbon atoms and preferably is an alkyl radical containing from 1 to 10 carbon atoms. More specifically, R is preferably a methyl, ethyl, n-propyl, isopropyl, n-butyl, isobutyl, t-butyl, sec-butyl, n-pentyl, 2-methylpentyl, 3-ethylpentyl, n-hexyl, 2-ethylhexyl or n-octyl radical. When R denotes an aryl radical, it preferably is a phenyl or substituted phenyl radical having the formula:

(III)

in which R' denotes an alkyl, alkoxy or perhalomethyl radical or a halogen atom, and n is an integer from 1 to 3.

R' preferably is a straight or branched chain alkyl radical containing from 1 to 4 carbon atoms, such as methyl, ethyl, n-propyl, isopropyl, n-butyl or sec-butyl radicals; an alkoxy radical containing from 1 to 4 carbon atoms in the alkyl moiety, such as methoxy, ethoxy or propyloxy radicals; a chlorine, bromine or fluorine atom; or a trichloromethyl or trifluoromethyl radical. Among the organic halides which may facilely be hydrocarbonylated by the process according to the invention, exemplary are methyl chloride, methyl bromide, methyl iodide, ethyl chloride, ethyl iodide, n-propyl chloride, n-propyl iodide, n-butyl chloride, isobutyl chloride and bromide, n-pentyl chloride and iodide, 2-methyl- or 3-methylbutyl chloride, bromide and iodide, benzyl chloride and iodide, p-methylbenzyl chloride and iodide, p- or m-chlorobenzyl chloride and bromide, p-trifluoromethylbenzyl chloride and iodide, and m- or p-methoxybenzyl chloride and iodide.

Any liquid carboxylic acid which is inert under the conditions of reaction can be employed as a reaction medium. Saturated aliphatic or alicyclic acids are preferably used. For practical reasons, acids which are liquid at ambient temperature and at normal pressure are also preferably employed. More particularly, the straight or branched chain alkanoic acids containing from 1 to 8 carbon atoms, such as formic acid, acetic acid, propionic acid, butyric acid, isobutyric acid, 3-methylbutanoic acid, 2-methylbutanoic acid, 2-ethylbutanoic acid, 2,2-dimethylbutanoic acid, pentanoic acid, 2-methylpentanoic acid, 5-methylpentanoic acid, hexanoic acid, 2-ethylhexanoic acid, or an alicyclic acid, such as cyclopentanecarboxylic acid, or methylcyclopentanecarboxylic acids, are advantageously employed. For reasons of convenience, it is preferable to use alkanoic acids containing from 1 to 4 carbon atoms. Acetic acid is particularly suitable. Although it is preferable to carry out the reaction in the absence of water, the latter does not interfere insofar as it does not represent more than 40% and preferably 20% of the volume of the carboxylic acid. It is thus possible to employ an anhydrous acid or an acid containing a small amount of water.

Any suitable basic agent can be used as an agent for neutralizing the hydrogen acid formed during the reaction. Preferably used are:

(a) Amines having the general formula:

  (IV)

in which $R_1$, $R_2$ and $R_3$, which may be identical or different, are each hydrogen, straight or branched chain alkyl radical, a cycloalkyl radical, an aryl radical, an alkylaryl radical, or an arylalkyl radical, with the proviso that no more than two of the radicals $R_1$, $R_2$ and $R_3$ can be a hydrogen atom; in the formula (IV) the moieties $R_1$, $R_2$ and $R_3$ preferably denote alkyl radicals containing from 1 to 30 carbon atoms (more preferably from 1 to 20), such as methyl, ethyl, n-propyl, isopropyl, n-butyl, isobutyl, tert-butyl, n-pentyl, isoamyl, n-hexyl, 2-ethylbutyl, n-heptyl, n-octyl, 2-ethylhexyl or dodecyl radicals, a cyclohexyl or cyclopentyl radical, a benzyl or 2-phenylethyl radical; or a phenyl, tolyl or xylyl radical. Exemplary of the amines of formula (IV), representative are methylamine, dimethylamine, trimethylamine, ethylamine, di- and triethylamine, diisopropylamine, triisopropylamine, diisobutylamine, di-n-pentylamine, N,N-diethylaniline, N,N-dimethylaniline, N-ethylaniline, benzylamine, n-butylcyclohexylamine, cyclohexylamine, n-decylamine and laurylamine. The secondary and tertiary amines are preferably used.

(b) Nitrogenous heterocyclic bases containing one or two ring nitrogen atoms, such as pyridine and substituted derivatives thereof containing 1 to 3 alkyl radicals containing from 1 to 4 carbon atoms, and piperidine and substituted derivatives thereof containing from 1 to 3 lower alkyl radicals. As exemplary such heterocyclic bases, representative are pyridine, α, β and γ-picoline, 2,3-lutidine, 2,4-lutidine, 3,5-lutidine, 2-ethylpyridine, 2,4,6-trimethylpyridine, piperidine, 1-n-butylpiperidine, 1,2-dimethylpiperidine, 1-methylpiperidine and 1-ethylpiperidine.

(c) Phosphines having the general formula:

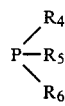  (V)

in which $R_4$, $R_5$ and $R_6$, which may be identical or different, are each a straight or branched chain alkyl radical containing from 1 to 30 carbon atoms, preferably 1 to 20 carbon atoms; a cycloalkyl radical containing from 5 to 6 carbon atoms; an arylalkyl radical containing from 1 to 4 carbon atoms in the alkyl moiety, with the proviso that no more than two of the radicals $R_4$, $R_5$ or $R_6$ can be an aryl radical, which is optionally substituted by one or more lower alkyl radicals; a radical having the general formula:

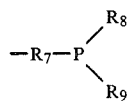  (VI)

in which $R_7$ is a straight or branched chain alkylene radical containing from 1 to 20 carbon atoms, preferably from 2 to 10 carbon atoms; $R_8$ and $R_9$ denote an alkyl radical, or a cycloalkyl, aryl or arylalkyl radical, such as those above-defined as $R_4$ to $R_6$. Exemplary of the radicals $R_4$, $R_5$ and $R_6$, representative are methyl, ethyl, n-propyl, isopropyl, n-butyl, isobutyl, tert-butyl, n-pentyl, isoamyl, n-hexyl, 2-ethylbutyl, n-heptyl, n-octyl, 2-ethylhexyl, dodecyl, cyclopentyl, cyclohexyl, methylcyclohexyl, benzyl, phenyl or tolyl radicals; $R_7$ advantageously is a methylene, ethylene, propylene, 1,4-butylene or hexamethylene radical. Exemplary of the phosphines of formula (V), representative are trimethyl phosphine, triethyl phosphine, tri-n-propyl phosphine, tri-n-butyl phosphine, methyldiethyl phosphine, ethyldi-n-propyl phosphine, methyldiisopropyl phosphine, triisopropyl phosphine, phenyldimethyl phosphine and 1,2-bis(diphenylphosphino)ethane.

(d) Alkali metal or alkaline earth metal salts of carboxylic acids having the general formula:

  (VII)

in which R denotes a valence bond or a mono- or polyvalent hydrocarbon moiety, M denotes an alkali metal, such as Na, K, Li, or an alkaline earth metal, and n is an integer from 1 to 3.

Advantageously, R denotes a saturated, straight or branched chain aliphatic hydrocarbon moiety containing from 1 to 30 carbon atoms; a saturated alicyclic hydrocarbon moiety containing from 5 to 6 carbon atoms; a mono- or polycyclic aromatic moiety; or a saturated arylaliphatic moiety. Preferably, R is an alkyl radical, such as methyl, ethyl, n-propyl, isopropyl, n-butyl, sec-butyl, isobutyl, t-butyl, n-pentyl, isoamyl, n-hexyl, 2-ethylbutyl, n-heptyl, n-octyl, 2-ethylhexyl, undecyl, dodecyl, stearyl, methylene, ethylene, trimethylene, tetramethylene, hexamethylene, phenyl, tolyls, xylyls, benzyl, cyclopentyl or cyclohexyl. Exemplary of the salts of formula (VII), representative are the sodium, potassium, lithium and calcium acetates, and Na, K, Li, Ca and Ba propionates, butyrates, pentanoates, hexanoates, 2-ethylhexanoates, octanoates, decanoates, undecanoates, stearates, cyclohexanoates, benzoates, toluates, phenylacetates and oxalates. It is also possible to employ mixtures of alkali metal or alkaline earth metal salts of mixtures of carboxylic acids with high carbon condensation, such as naphthenic acids. Among these alkali metal salts, those derived from the acid employed as the reaction medium are preferably selected for practical reasons.

(e) Phosphonium or ammonium carboxylates having the general formula:

(VIII)

in which R and n are as defined above, in connection with formula (VII), Z denotes a nitrogen or phosphorus atom, R", R''', R'''' each denote a hydrogen atom when Z denotes a nitrogen atom, or hydrocarbon radicals which may be identical or different. Preferably, R", R''', R'''' and R''''' are straight or branched chain alkyl radicals containing from 1 to 30 carbon atoms (more preferably from 1 to 20), such as methyl, ethyl, n-propyl, isopropyl, n-butyl, isobutyl, tert-butyl, n-pentyl, isoamyl, n-hexyl, 2-ethylbutyl, n-heptyl, n-octyl, 2-ethylhexyl, dodecyl, cyclopentyl, cyclohexyl or methylcyclohexyl radicals; cycloalkyl radicals containing from 5 to 6 ring carbon atoms, such as cyclopentyl, cyclohexyl or methylcyclohexyl radicals; aryl radicals optionally substituted by one or more lower alkyl radicals (containing from 1 to 4 carbon atoms), such as phenyl, tolyl or xylyl radicals; arylalkyl radicals containing from 1 to 4 carbon atoms in the alkyl moiety, such as benzyl or 2-phenylethyl radicals. Exemplary of such salts, representative are ammonium acetate, propionate, 2-ethylhexanoate, stearate and benzoate; tetramethylphosphonium, tetraethylphosphonium and methyltributylphosphonium acetates, tetraethylammonium, tetrabutylammonium and methyltributylammonium acetate and tetraphenylphosphonium propionate.

When alkali metal or alkaline earth metal or ammonium carboxylates are employed, these may be charged in a preformed state or alternatively may be formed "in situ" by introducing the corresponding base into the carboxylic acid employed as the reaction medium. Because of the nature of the reaction medium, carboxylates are preferably used and in particular the alkali metal or alkaline earth metal or ammonium salts derived from the carboxylic acid thus employed, or from any other carboxylic acid; hence, salts of carboxylic acids which are not liquid under the reaction conditions, such as octanoates or benzoates, may be employed.

The amount of agent for neutralizing the hydrogen acids, expressed as molar equivalent of base per mole of organic halide, may vary over wide limits. Preferably, this amount is at least close to the stoichiometric amount, that is to say, one molar equivalent of base per mole of organic halide. Although there is no critical upper limit to this amount, the use of a base molar equivalent/mole of organic halide ratio above 3 does not result in any particular advantage. Preferably, the neutralizing agent represents from 0.9 to 2.5 molar equivalents per mole of organic halide, and preferably from 1 to 2 molar equivalents.

The catalysts used may be derivatives of transition metals typically employed in hydrocarbonylation reactions, such as those mentioned in published French patent application 73/46,069 referred to hereinabove. Preferably, carbonyl derivatives are used of the metals of Group VIII of the Periodic Table of Elements [cf. Handbook of Chemistry and Physics, 53rd edition, published by "The Chemical Rubber Company" (1972-73)-]and particularly of iron, cobalt and nickel. Preferably used are dicobaltoctacarbonyl, tetracobaltdodecacarbonyl and the salts of tetracarbonylcobaltate($-1$) hydride [$HCo(CO)_4$], and especially those derived from alkali metals or alkaline earth metals, ammonium or phosphonium, such as sodium, potassium, lithium, calcium, ammonium, tetraethylammonium, or methyltriphenylphosphonium tetracarbonylcobaltates($-1$). It is also possible to use mixtures of these cobalt carbonyls.

The amount of catalyst, expressed as gram-atoms of metal per mole of organic halide, may also vary over wide limits. Thus, and this constitutes one of the advantages of the process according to the invention, the amount of hydrocarbonylation catalyst can represent only 0.001 (preferably 0.01) gram-atom of metal per mole of organic halide. Although there is no critical upper limit on the amount of catalyst, it is not necessary to exceed 0.5 gram-atom of cobalt per mole of organic halide; a quantity below or equal to 0.35 gram-atom per mole of organic halide is generally sufficient. It would naturally be possible to resort to amounts of catalyst outside the limits defined above without departing thereby from the scope of the present invention.

The temperature at which the reaction is carried out depends to a large extent on the substrate subjected to the hydrocarbonylation. In general, this temperature ranges from 20° to 150° C.; however, in the case of the hydrocarbonylation of benzyl halides it is preferable not to exceed a temperature of 100° C. Overall, the reaction temperature preferably ranges from 50° to 120° C.

The total pressure of carbon monoxide and hydrogen employed to ensure that the reaction takes place may also vary over wide limits. It may thus be at least 1 MPa. Although it may reach the values usually employed in this type of reaction, it is not necessary to resort to pressures above 12 MPa and preferably 11 MPa. This constitutes another advantage of the process according to the invention. In general, a total pressure in a range from 2 to 10 MPa is suitable.

The amounts of carbon monoxide and hydrogen employed must be sufficient to ensure complete conversion of the organic halide. Beyond these amounts there are no critical upper limits.

The composition of the gaseous mixture of carbon monoxide and hydrogen is not critical and also may vary over wide limits. An excess of either constituent of the mixture can be employed, this being immaterial. Thus, the molar ratio $CO/H_2$ may vary from 1/10 to 10 and preferably from ¼ to 4.

From a practical standpoint the process according to the invention does not present any particular difficulties and can readily be employed industrially, especially in a continuous manner. As a general rule it is sufficient to charge the carboxylic acid, the organic halide, the catalyst and the agent for neutralizing the hydrogen acids into a pressure-resistant apparatus, then to purge the latter with a stream of $CO/H_2$, to establish an adequate pressure of $CO/H_2$ and to bring the contents of the apparatus to the selected temperature. When $CO/H_2$ absorption ceases, the reaction mass is cooled to ambient temperature and the aldehyde formed is recovered by conventional techniques, for example, by distillation. The carboxylic acid containing the catalyst may be recycled to a new hydrocarbonylation operation. In the case of the hydrocarbonylation of benzyl halides it is preferable to charge the latter into the apparatus by means of a pressure of carbon monoxide after the appropriate temperature and pressure have been established. The introduction of benzyl halide may be carried out once or several times, and either continuously or non-continuously.

The reaction time depends upon the conditions selected.

In order to further illustrate the present invention and the advantages thereof, the following specific examples are given, it being understood that same are intended only as illustrative and in nowise limitative.

EXAMPLE 1

The following materials were charged into a 120 ml tantalum autoclave stirred by shaking:
(i) 50 ml of acetic acid;
(ii) 2.02 g of methyl chloride (40 mmol);
(iii) 4.1 g of sodium acetate (50 mmol); and
(iv) 0.646 g of dicobaltoctacarbonyl (3.8 mg-atom).

The autoclave was purged with a gaseous stream of a mixture of $CO/H_2$ (1 mole/2moles), was closed, and a $CO/H_2$ pressure of 7.9 MPa was established. Its contents were then brought to 80° C. by means of a ring furnace. The pressure was maintained constant and equal to 9.5 MPa by a continuous supply of an equimolar mixture of $CO/H_2$. After 2 hours, 10 min under these conditions the absorption of $CO/H_2$ ceased. The reaction mass was cooled to 20° C. and the autoclave was degassed. The reaction mixture was analyzed by gas phase chromatography (GPC). It was found that all of the methyl chloride had been converted. 1.7 g of acetaldehyde had been formed, representing a yield of 97% based on the methyl chloride charged (RY).

EXAMPLES 2 to 3

The procedure of Example 1 was repeated, except that the methyl chloride was replaced with ethyl iodide (6.24 g) (Example 2) and n-butyl iodide (7.36 g) (Example 3), everything else remaining the same.

The following Table I reports the results obtained:

TABLE I

| EXAMPLES | Organic halide C % (1) | Time (in min) | RY of aldehyde (%) |
|---|---|---|---|
| 2 | ethyl iodide 100 | 80 | propanal 87% |
| 3 | n-butyl iodide 100 | 110 | pentanal 86% |

(1) conversion.

EXAMPLE 4

Example 1 was repeated, except that the methyl chloride was replaced by methyl iodide (5.68 g), all else remaining the same except that the pressure was maintained at 9.5 MPa by a continuous feed of a $CO/H_2$ mixture, ½ on a molar basis. The absorption period was 80 minutes under these conditions, the conversion of methyl iodide was 100% and the RY of acetaldehyde was 95%.

EXAMPLES 5 to 7

The procedure of Example 4 was repeated, except that the amount of dicobaltoctacarbonyl was varied and the amount of sodium acetate was raised to 8.2 g (100 mmol). The following Table II reports the results obtained:

TABLE II

| EXAMPLES | $CO_2(CO)_8$ | TIME (min) | T (%) | RY of acetaldehyde (%) |
|---|---|---|---|---|
| 5 | 321 mg 1.88 mg-at | 100 | 100 | 95 |
| 6 | 637 mg 3.7 mg-at | 40 | 100 | 95 |
| 7 | 1.266 mg 7.4 mg-at | 25 | 100 | 95 |

EXAMPLE 8

The following materials were charged into a 250 cc stainless steel autoclave stirred by a shaker device and heated by a ring furnace:
(i) Acetic acid: 80 ml;
(ii) Sodium acetate: 6.31 g (77 mmol); and
(iii) Dicobaltoctacarbonyl: 2.07 g (12.1 mg-at).

After the autoclave had been purged an equimolar mixture of $CO/H_2$ was introduced up to a pressure of 5.2 MPa and then the temperature of the contents of the autoclave was adjusted to 80° C. Into a second 125 ml autoclave were charged 10.12 g of benzyl chloride (80 mmol) dissolved in 20 ml of acetic acid and 14 MPa of hydrogen. When the temperature reached 80° C. in the first autoclave it was connected to the second such as to charge the acetic acid solution of benzyl chloride. The pressure was maintained at 9.5 MPa by continuous feed of an equimolar mixture of $CO/H_2$. After 30 min absorption ceased. The reaction mixture was treated and analyzed as in Example 1. The conversion of benzyl chloride was 96% and the yield of phenylacetaldehyde based on the benzyl chloride charged was 87%.

EXAMPLE 9

Example 8 was reproduced, except that the amount of $Co_2(CO)_8$ was increased from 2.07 g to 2.16 g (12.6 mg-at) and the temperature from 80° to 100° C. The reaction time was 20 min, the conversion of benzyl chloride 65% and the RY 45%, which corresponded to a phenylacetaldehyde yield of 69.2% based on the benzyl chloride converted (CY).

EXAMPLE 10

The following materials were charged into an 80 ml stainless steel autoclave equipped as described above:
(i) Acetic acid: 32 ml;
(ii) Triethylamine: 3.05 g (30 mmol);
(iii) $CO_2(CO)_8$: 1.37 g (8 mg-at); and
(iv) Benzyl chloride: 3.3 g (26 mmol) in a glass tube of a height greater than the level of the liquid present in the autoclave.

After the latter had been purged, 7.9 MPa of an equimolar mixture of $CO/H_2$ were introduced. The temperature was then raised to 80° C., shaking was commenced and the pressure was maintained at 9.5 MPa as previously. After 40 min absorption ceased. The reaction mixture was treated and analyzed as in the previous examples. The conversion of benzyl chloride was 100% and the RY of phenylacetaldehyde 80%.

EXAMPLE 11

Example 10 was repeated, except that the triethylamine was replaced by 3.18 g of calcium acetate (20 mmol) and the amount of $Co_2(CO)_8$ brought back to 1.12 g (6.6 mg-at). The conversion of benzyl chloride was 60% for a time of 30 min and the RY 65% (i.e. a CY of 89%).

EXAMPLES 12 to 16

Five tests, the conditions and the results of which are reported in the following Table III were carried out in the autoclave described in Example 10 by following the same operating procedure (in all cases 40 mmol of benzyl chloride were charged and the temperature was 80° C).

TABLE III

| EX-AMPLES | Medium (in ml) | | Sodium acetate (in mmol) | $Co_2(CO)_8$ (in mg-at of Co) | Pressure (in MPa) | Time (in min) | C (%) | RY (%) | CY (2) % |
|---|---|---|---|---|---|---|---|---|---|
| 12 | CH₃COOH | (45) | 50 | 3.27 | 9.5 | 70 | 81 | 71 | 87.6 |
| 13 | CH₃COOH water | (30) (20) | 42 | 3.8 | 9.5 | 140 | 62 | 34 | 54.8 |
| 14 | CH₃COOH water | (40) (10) | 42 | 3.2 | 9.5 | 60 | 67 | 57 | 85 |
| 15 | CH₃COOH | (45) | 40 | 3.5 | 3 | 40 | 54 | 34 | 62.9 |
| 16 (1) | CH₃COOH | (45) | 40 | 3.5 | 6 | 100 | 65 | 54 | 83 |

(1) A pressure of 6 MPa was established by means of a CO/H₂ mixture, 2/1 on a molar basis, and then maintained by means of an equimolar mixture of CO/H₂. (2) Yield of phenylacetaldehyde based on the benzyl chloride converted.

EXAMPLE 17

The procedure of Example 1 was repeated, under the following conditions:
(i) Benzyl chloride: 3.26 g (25.8 mmol);
(ii) Acetic acid: 32 ml;
(iii) Diisopropylamine: 3.04 g (30.1 mmol);
(iv) $Co_2(CO)_8$: 1.34 g (7.8 mg-at);
(v) Temperature: 80° C.;
(vi) Total pressure: 9.5 MPa; and
(vii) CO/H₂: 1.

Under these conditions absorption ceased after 20 minutes. All of the benzyl chlordie had been converted and chromatographic determination demonstrated a phenylacetaldehyde yield of 85%.

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an aldehyde, comprising catalytically hydrocarbonylating an organic halide having the general formula $$R—CH_2X \qquad (II)$$

in which R is a hydrogen atom, an alkyl radical or an aryl radical and X denotes a halogen atom with gaseous admixture of hydrogen and carbon monoxide in the presence of a basic neutralizing agent for the hydrogen acid produced thereby, said hydrocarbonylation being carried out in an inert, liquid carboxylic acid reaction medium.

2. The process as defined by claim 1, said inert, liquid carboxylic acid reaction medium comprising a saturated aliphatic or alicyclic carboxylic acid.

3. The process as defined by claim 2, said inert, liquid carboxylic acid reaction medium comprising a straight or branched chain alkanoic acid having from 1 to 8 carbon atoms.

4. The process as defined by claim 3, said alkanoic acid having from 1 to 4 carbon atoms.

5. The process as defined by claim 4, said alkanoic acid comprising acetic acid.

6. The process as defined by claim 2, said inert, liquid carboxylic acid reaction medium comprising a cycloalkanecarboxylic acid.

7. The process as defined by claim 1 for the preparation of an aldehyde having the general formula:

$$R—CH_2—CHO \qquad (I)$$

wherein R is hydrogen, alkyl or aryl, comprising catalytically hydrocarbonylating an organic halide having the general formula:

$$R—CH_2—X \qquad (II)$$

wherein R is as above defined and X is chloro, bromo or iodo.

8. The process as defined by claim 7, wherein said aldehyde and halide having the formulae (I) and (II), R is a straight or branched chain alkyl radical having from 1 to 20 carbon atoms, phenyl, or a substituted phenyl radical having the general formula:

(III)

wherein R; is alkyl, alkoxy, perhalomethyl or halo, and n is an integer from 1 to 3.

9. The process as defined by claim 8, wherein R is a straight or branched chain alkyl radical having from 1 to 10 carbon atoms.

10. The process as defined by claim 9, wherein said aldehyde (I) comprises acetaldehyde, propanal, pentanal or phenylacetaldehyde and said halide (II) comprises methyl, ethyl, n-butyl or benzyl chloride or iodide.

11. The process as defined by claim 1, wherein the hydrocarbonylation catalyst comprises a transition metal compound.

12. The process as defined by claim 11, wherein the hydrocarbonylation catalyst comprises a carbonyl compound of a Group VIII metal.

13. The process as defined by claim 12, wherein the hydrocarbonylation catalyst comprises a carbonyl compound of cobalt.

14. The process as defined by claim 13, said catalyst comprising dicobaltoctacarbonyl, tetracobaltdodecacarbonyl, or a salt of tetracarbonylcobaltate($-1$) hydride.

15. The process as defined by claim 11, wherein the amount of catalyst, expressed as gram-atoms of metal per mole of organic halide, ranges from 0.001 to 0.5 gram-atoms per mole.

16. The process as defined by claim 1, said neutralizing agent comprising an amine having the general formula:

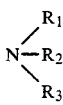 (IV)

wherein $R_1$, $R_2$ and $R_3$, which may be identical or different, are each hydrogen, a straight or branched chain alkyl radical, a cycloalkyl radical, an aryl radical, an alkylaryl radical, or an arylalkyl radical, with the proviso that no more than two of the radicals $R_1$, $R_2$ and $R_3$ can be hydrogen.

17. The process as defined by claim 1, said neutralizing agent comprising a nitrogenous heterocyclic base containing one or two ring nitrogen atoms.

18. The process as defined by claim 1, said neutralizing agent comprising a phosphine having the general formula:

 (V)

wherein $R_4$, $R_5$ and $R_6$, which may be identical or different, are each a straight or branched chain alkyl radical, a cycloalkyl radical, an arylalkyl radical, an aryl radical, with the proviso that no more than two of the radicals $R_4$, $R_5$ and $R_6$ can be aryl radicals, or substituted such aryl radicals bearing one or more lower alkyl substituents, or a radical having the general formula:

 (VI)

wherein $R_7$ is a straight or branched chain alkylene radical, and $R_8$ and $R_9$ are as above defined for $R_4$, $R_5$ and $R_6$.

19. The process as defined by claim 1, said neutralizing agent comprising an alkali or alkaline earth metal salt of a carboxylic acid having the general formula:

 (VII)

wherein R is a valence bond or a mono- or polyvalent hydrocarbon, M is an alkali or alkaline earth metal, and n is an integer from 1 to 3.

20. The process as defined by claim 1, said neutralizing agent comprising a phosphonium or ammonium carboxylate having the general formula:

 (VIII)

wherein R is a valence bond or a mono- or polyvalent hydrocarbon, Z is a nitrogen or phosphorus atom, R'', R''', R'''' and R''''' are each hydrogen when Z is nitrogen, or, when Z is phosphorus, are each identical or different hydrocarbon radicals, and n is an integer from 1 to 3.

21. The process as defined by claim 1, said neutralizing agent comprising sodium, potassium or calcium acetate, triethylamine or diisopropylamine.

22. The process as defined by claim 1, wherein the amount of neutralizing agent ranges from 0.9 to 2.5 molar equivalents per mole of organic halide.

23. The process as defined by claim 1, said hydrocarbonylation being carried out at a temperature of from 20° to 150° C.

24. The process as defined by claim 1, wherein the total pressure of the gaseous $CO/H_2$ admixture in said hydrocarbonylation reaction ranges from 1 to 12 MPa.

25. The process as defined by claim 24, wherein the molar ratio of the carbon monoxide to the hydrogen in said gaseous admixture ranges from 1/10 to 10.

* * * * *